United States Patent [19]

Neti et al.

[11] 4,051,006
[45] Sept. 27, 1977

[54] PORTABLE ELECTROCHEMICAL CELL STRUCTURE

[75] Inventors: Radhakrishna Murty Neti, Brea; Ray Lawrence Roggenkamp, Fountain Valley, both of Calif.

[73] Assignee: Beckman Instruments, Inc., Fullerton, Calif.

[21] Appl. No.: 669,072

[22] Filed: Mar. 22, 1976

[51] Int. Cl.² ............................................. G01N 27/46
[52] U.S. Cl. ................................ 204/195 P; 204/1 T;
427/125; 427/404; 427/405
[58] Field of Search .................... 204/1 T, 1 N, 1 K,
204/195 R, 195 P

[56] References Cited
U.S. PATENT DOCUMENTS

| | | | |
|---|---|---|---|
| 3,000,804 | 9/1961 | Cahoon et al. | 204/195 F |
| 3,088,905 | 5/1963 | Glover | 204/195 P |
| 3,149,921 | 9/1964 | Warner | 204/1 T |
| 3,244,607 | 4/1966 | Leonard et al. | 204/195 T |
| 3,622,487 | 11/1971 | Chand et al. | 204/1 N |
| 3,676,220 | 7/1972 | Ward | 204/195 P |
| 3,776,832 | 12/1973 | Oswin et al. | 204/195 R |
| 3,824,167 | 7/1974 | Oswin et al. | 204/195 R |
| 3,855,096 | 12/1974 | Bergman | 204/195 P |

*Primary Examiner*—T. Tung
*Attorney, Agent, or Firm*—Robert J. Steinmeyer; Paul R. Harder; Donald A. Streck

[57] ABSTRACT

An electrochemical detection cell particularly suited for portable applications because of its small size and low cost. An enclosure is provided having two membrane surfaces. Electrodes are suspended internally between the two membranes supported by an electrochemically inert hydrophilic material containing an electrolyte solution. An improved electrode structure for use within the cell is disclosed.

6 Claims, 5 Drawing Figures

PORTABLE ELECTROCHEMICAL CELL STRUCTURE

BACKGROUND OF THE INVENTION

The present invention relates to electrochemical cells and, more particularly, to portable cells adapted for the detection and measurement of selected gases in the atmosphere.

The increasing concern with pollutants, in both the atmosphere and specfic breathing environments, has caused a sudden demand to supplement conventional laboratory apparatus for detecting and measuring components in a gaseous mixture, such as air, with more portable devices. For example, carbon monoxide has heretofore been measured using infrared techniques. Such apparatus is not readily adaptable for wear by mine workers or even placement on mine vehicles. Electrochemical techniques present a potential solution but not, however, without problems. Since the use of aqueous electrolytes is employed in electrochemical detection and measurement, there is a safety factor to be considered, particularly when the apparatus is to be worn on the person. Also, electrochemical reactions develop a current signal of very small magnitude when employed in a detector sized to be easily carried or worn. This can result in a requirement for larger heavier amplification means as well as causing an inherent lack of stability and response.

As described herein, the present invention is directed to the measurement of carbon monoxide. As will be understood by those skilled in the art, a cell of the type herein described could by used equally well in the detection of numerous gases and, alternatively, could be employed as a fuel cell.

Electrochemical determination of carbon monoxide is one of the most sensitive methods of detection. Electrodes used are formed from the noble metals, e.g. platinum or gold. The electrolyte used is usually sulfuric or phosphoric acid. In one apparatus, a suitable potential is applied between the anode (working electrode) and the cathode (counter electrode). This arrangement permits the amperometric detection of the resulting current flow between anode and cathode. In another commonly used technique, an additional (reference) electrode is employed. In this manner, the presence of carbon monoxide may be detected potentiostatically. In such apparatus, the reference electrode is a hydrogen electrode. Typical prior art cells include those of Niedrach et al. (U.S. Pat. No. 3,432,355) and Oswin et al. (U.S. Pat. No. 3,776,832). In the patent of Niedrach et al. and an article by Niedrach and Alford "A New High-Performance Fuel Cell Employing Conducting-Porous-Teflon Electrodes and Liquid Electrolytes," *Journal of the Electrochemical Society*, Vol. 112, No. 2, Feb. 1965, page 117, the authors describe the construction of the electrodes used in their cell by the technique of forming a platinum black and polytetrafluoroethylene suspension on a polytetrafluroethylene membrane at an elevated temperature to cause the bonding of the polytetrafluoroethylene and platinum black. A platinum screen is then disposed between two such coated membranes with the membrane material on the outsides and the total assembly is sintered together at an elevated temperature, and preferably under pressure, to form a unitary element. According to both these prior art references, one surface of the electrode is exposed to the electrolyte and the opposite is exposed to the gas being tested. In order for the electrochemical reaction to take place between electrodes thus disposed, the electrolyte must disperse through the electrode or, alternatively, the working gas must disperse through the electrode. In either case, movement through the electrode is required and the surface available for electrochemical reaction per unit area of electrode is minimal because of the method of forming.

While the cell structures are somewhat identical in both cases, the cell of Niedrach et al. is directed to a fuel cell application while that of Oswin et al. is directed toward electrochemical detection of noxious gases in the atmosphere. A cell such as that described by Oswin et al. can only be operated in one position and is not, therefore, readily adpated for use as a personal monitor such as in mines, etc. Moreover, these prior art electrodes are not only sensitive to carbon monoxide but also NO, $SO_2$, $H_2S$, unsaturated hydrocarbons and other organics. If the ambient air being tested contains gases other than pure reference gas, the observed reading due to carbon monoxide is decreased in relation to its sensitivity and concentration. The interference by these other gases occurs in two ways. When entering through the sensitive (inlet) side adjacent the anode, CO and the other gases to which the electrode will react cause a positive going signal depending upon their relative proportions. The same gases if allowed to come in contact with the other (counter) electrode will result in a signal of opposite polarity. This problem was realized by others who suggested that in apparatus employing a reference electrode such as that of Oswin et al., a reference atmosphere be provided by maintaining an atmosphere of pure air over the reference electrode. This technique also tends to make the detector not portable and, further, provides a sensor with a data output that is not correlatable with other known standard methods, such as infrared detection of carbon monoxide.

Thus, it is the object of the present invention to provide a truly portable electrochemical cell having a high current signal for its size capable of either two electrode amperometric detection or three electrode potentiostatic detection.

SUMMARY

The foregoing objective has been accomplished in the present invention by disposing improved platinum black electrodes in an electrochemically inert enclosure having high porosity membrane covered openings. The enclosure is filled with an electrochemically inert hydrophillic material such as glass wool containing the electrolyte dispersed throughout. The anode is positioned closely adjacent one membrane but in noncontacting relationship with the membrane. The test gas is brought in contact with the anode membrane under a slight positive pressure which causes the test gas to permeate the membrane and contact the anode in the presence of the electrloyte. Contaminating gases produced during the electrochemical reaction at the anode are free to pass out of the cell through the other membrane. The improved electrode for use in the cell is produced by pressing platinum black onto a platinum-/irridium screen and coating this base structure with a platinum black and polytetrafluoroethylene suspension which is then dried at a temperature below the sintering temperature of the polytetrafluoroethylene, and without pressure to create a high surface area working surface. A thin protective overcoating of polytetrafluoroethylene suspension is then added and air dried.

DESCRIPTION OF THE PREFERRED EMBODIMENTS

Figure 1:
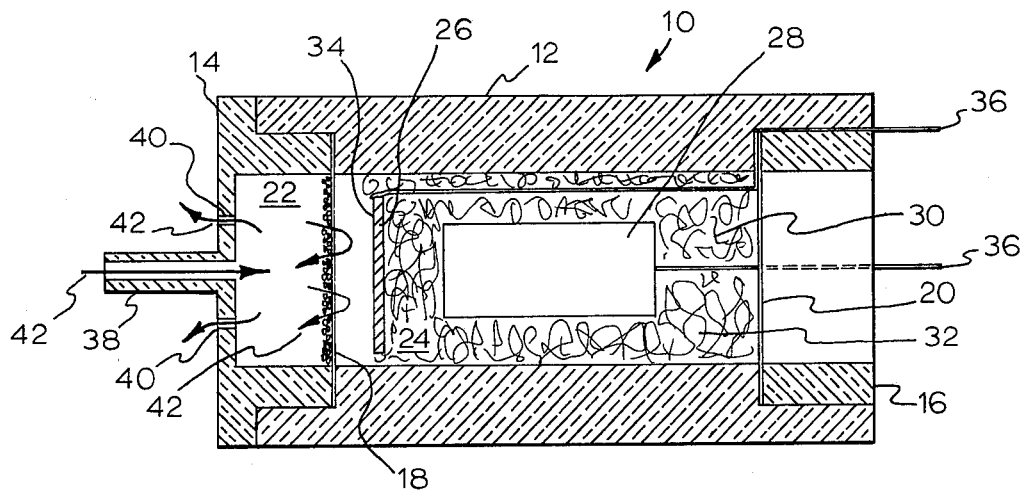
FIG. 1 is a cross section through a cell according to the present invention employing two electrodes and having a scrubbing interface on one membrane.

Referring first to FIG. 1, an electrochemical detection cell 10, functioning as an amperometric cell, as is well known in the art, is shown having a cylindrical body 12. A cap 14 is affixed to one end of body 12 and a collar 16 is affixed to the opposite end. Body 12, cap 14, and collar 16 are of electrochemically inactive material such as polytetrafluoroethylene. A first membrane 18 is held in place across cylindrical body 12 by cap 14. A second membrane 20 is held in place across the opposite end of cylindrical body 12 by collar 16. When disposed and held in place as shown in FIG. 1, first membrane 18 in combination with cap 14 defines a first enclosure 22. First membrane 18 and second membrane 20 in conjunction with body 12 define a second enclosure 24. Membranes 18 and 20 are of porous polytetrafluoroethylene such as that sold by W. L. Gore and Associates under the trademark Gore-Tex. Gore-Tex No. 4 and No. 3 have been found to work exceptionally well in this application and have (according to the manfacturer) a pore size of 0.1 to 10 microns and are of a high pore density. An anode 26 and a cathode 28 are disposed within second enclosure 24 and held in place by an electrochemically inert hydrophilic filler material such as glass wool 30. Glass wool 30 is saturated with an appropriate electrolyte 32 such as sulfuric or phosphoric acid. Anode 26 should be disposed with its working surface closely adjacent but not touching first membrane 18. The "working surface" is described more fully in conjunction with the description of the method of fabrication of an improved electrode for incorporation in the cell as is contained hereinafter. The placement of the cathode 28 within glass wool 30 and electrolyte 32 is relatively unimportant but has been found to work well when placed approximately in the center of the body 12 as shown to prevent touching other electrical surfaces in the event of shock or vibration. Wires 36 connected to electrodes 26 and 28, as will be hereinafter described, pass to the outside of cell 10 to allow electrical connection to the electrodes 26 and 28. Cap 14 is fitted with an inlet pipe 38 and outlet holes 40. The total cross-sectional area of outlet holes 40 should be somewhat less than the cross-sectional area of inlet pipe 38. In this manner, when the gas to be tested, e.g. atmosphere, is introduced through inlet pipe 38 under slight pressure as with a small pump (not shown), the difference in flow rates through inlet pipe 38 and outlet holes 40 will cause a very slight positive pressure within enclosure 22. This very slight pressure within first enclosure 22 is sufficient to permit the test gas 42 to permeate first membrane 18 and contact the working surface 34 of anode 26 in the presence of electrolyte 32 causing the desired electrochemical reaction. Sufficient pressure should be generated within first enclosure 22 only to cause the test gas 42 to enter second enclosure 24 to a point adjacent anode electrode 26 and not sufficient to cause the test gas 42 to pass through body 12. Second membrane 20 provides a path for gases generated as a byproduct of the electrochemical reactions in second enclosure 24 to exit to prevent contamination and an attendant reduction in response of cell 10. Thus, membranes 18, 20 allow passage of gases into and out of second enclosure 24 while maintaining electrolyte 32 therein.

Additionally, a layer of silver oxide 43, preferably argentous oxide, is attached to first membrane 18 on the surface internal to first enclosure 22 to scrub out the interfering gases such as $X_2$, $H_2S$, $SO_2$, $O_3$, $NO$, and $NO_2$ to make the system sensitive only to CO. The temperature sensitivity of the cell 10 can, of course, be compensated electronically with a thermistor by techniques well known in the art.

Figure 2:
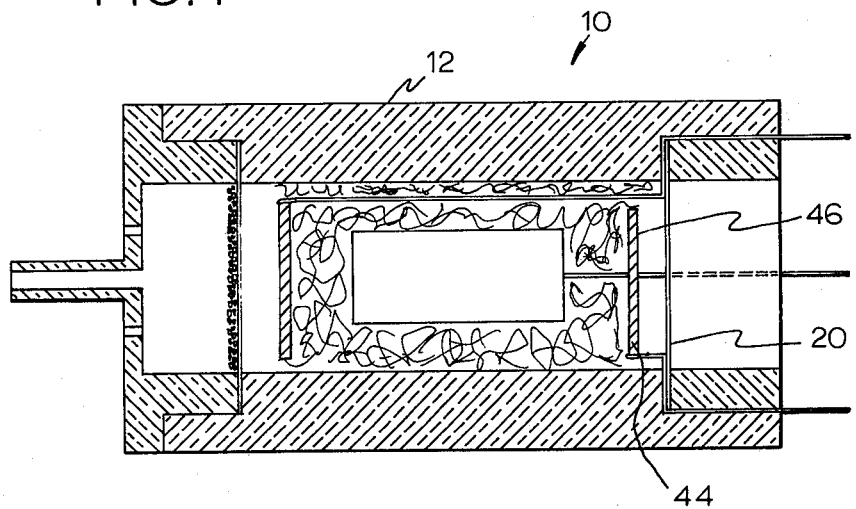
FIG. 2 is a cross section through a cell according to the present invention employing three electrodes and having a scrubbing interface on one membrane.

Referring to FIG. 2, a detection cell 10 is illustrated which is identical to the cell of FIG. 1 except that there is disposed within second enclosure 24 a reference electrode 44 for potentiostatic measurements. When a reference electrode 44 is employed, the working surface 46 of reference electrode 44 should be disposed closely adjacent second membrane 20 without touching it. It should be noted that the recessed placement of second membrane 20 within collar 16 as shown in FIGS. 1–4 provides protection for the membrane 20.

Figure 3:
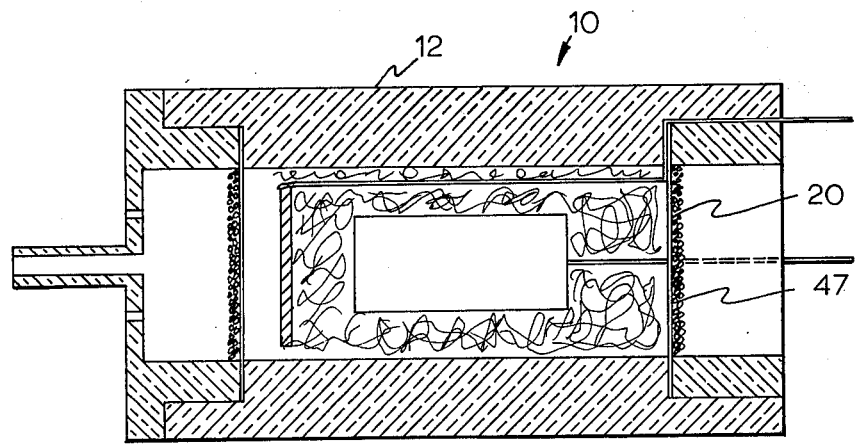
FIG. 3 is a cross section through a cell according to the present invention employing two electrodes and having a scrubbing interface on both membranes.
Figure 4:
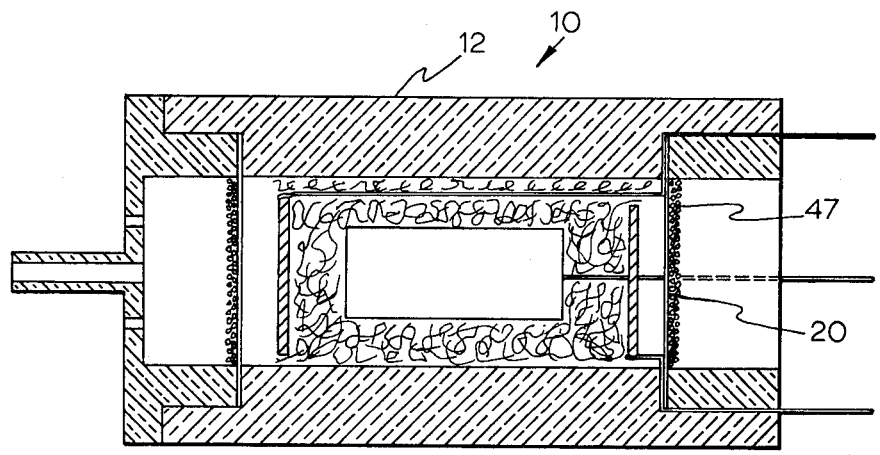
FIG. 4 is a cross section through a cell according to the present invention having three electrodes and having a scrubbing interface on both membranes.
Figure 5:
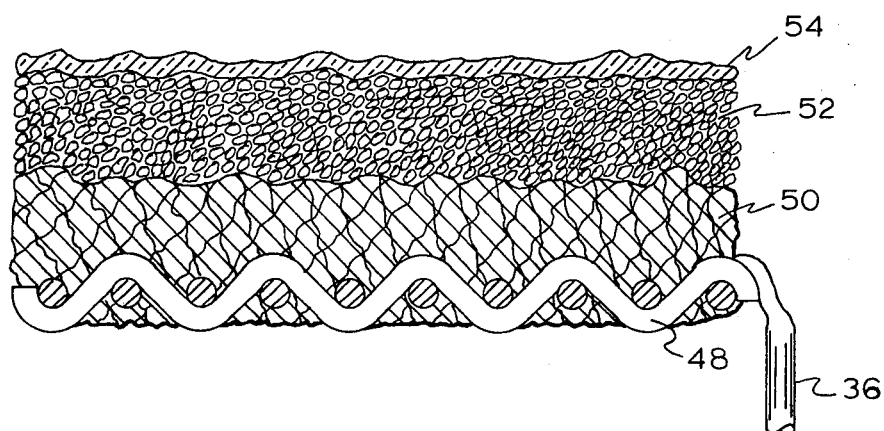
FIG. 5 is a cross section through an electrode as employed in the present invention.

Neither the two electrode cell 10 of FIG. 1 nor the three electrode cell of FIG. 2 are considered to be preferred embodiments. The former is adapted for amperometric detection and the latter is adapted for potentiostatic detection. It is preferred to employ a second scrubber or membrane as shown in FIG. 3 and FIG. 4. As shown, a layer 47 of palladium on carbon is incorporated on the outer surface of second membrane 20 to scrub interference gases before they reach second enclosure 24 and, in particular, reference electrode 44, while allowing gases generated internally within second enclosure 24 to escape. If this is not done, accumulated products may suppress the true response to carbon monoxide. An alternative, but not preferred approach to solving this same problem is to use a relatively low porosity Teflon membrane as layer 47 adjacent second membrane 20 thereby attenuating the interference of the common gases by inhibiting their entrance to second enclosure 24 of cell 10.

In a cell having an aqueous electrolyte, contained at least partially by a membrane, it is common to have a certain amount of electrolyte loss over a period of time. If the porosity of the membrane is reduced to a point where virtually no loss occurs, the sensitivity of the cell suffers. Therefore, it is usual to employ a bubbler in conjunction with the cell. Moreover, when operating in the 1000 ppm range with a high porosity membrane, the cell soon becomes saturated and must be cylced in its operation to allow periods of revitalization for the cell. The extreme sensitivity of the present cell allows the elimination of both these problems. By making first membrane 18 and second membrane 20 of a thick highly porous polytetrafluoroethylene material or the like, being about one millimeter thick and having a pore size of 1 micron or less, the electrolyte is contained within second enclosure 24 without the use of a bubbler. Moreover, a cell so constructed has been run for extended periods of time sampling in the 1000 ppm range with a satisfactory sensitivity and no apparent saturation.

To allow full performance in a small cell, as is possible with the present invention, the electrodes employed in the present invention were prepared according to a method yielding superior results to that of the electrodes described according to the techniques of Niedrach et al. The sintering technique of Niedrach et al., particularly when coupled with the pressing of the electrodes as suggested therein, yields a membrane covered electrode with a diminished catalytic surface area for interaction between the electrolyte and the test gas. When building and testing cells according to the present invention with electrodes prepared according to the method which hereinafter follows, it was found that good response and repeatability were attained with electrodes measuring approximately one centimeter in diameter. Therefore, preparation will be described hereinafter in relation to such an electrode. The preparation of larger electrodes can be extrapolated from that description.

A one centimeter diameter noble metal screen 48 is cut and a connecting wire 36 is welded thereto. A 52 mesh screen was found to work quite well; however, the screen could be as low as 30 mesh or up to 200 mesh. On the low end, one is limited by the screen's ability to support the material. On the high end, resistance and cost become a major factor. The screen 48 should be a noble metal. Substantially pure platinum was tried and found acceptable; however, the preferred embodiment as presently contemplated employs a screen of 90% platinum 10% irridium. Two to 20 milligrams of platinum black 50 are pressed onto screen 48 at ambient temperature with a pressure of 500 to 3,000 psi. The screen 48 containing pressed platinum black 50 is subsequently coated with an aqueous suspension of platinum black and polytetrafluoroethylene. This coating 52 will take anywhere from 5 to 50 milligrams of suspension and can be brushed or spread on. The polytetrafluoroethylene to water suspension ratio can be from 1:5 to 1:50 with 1:20 being preferred. The coating 52 of suspension of platinum black and polytetrafluoroethylene is dried at a temperature of 80° to 200° C which is below the sintering temperature of the polytetrafluoroethylene. The platinum black and polytetrafluoroethylene coating 52 is then protected by overcoating with a thin layer (1 to 2 milligrams) of polytetrafluoroethylene suspension 54 and drying it in air. As opposed to the sintering and pressing technique of the prior art, this method results in a non-membrane covered irregular working surface containing a much higher surface area of the platinum black catalyst upon which the electrochemical reaction can take place.

Having thus described our invention, we claim:

1. An electrochemical cell comprising:
   a. a body having a space therein and two openings into said space, said body being of an electrochemically inert material;
   b. a first membrane disposed to cover one of said two openings in said body, said first membrane being of a highly porous electrochemically inert material;
   c. a second membrane disposed to cover the other of said two openings in said body, said second membrane being of highly porous electrochemically inert material;
   d. a first electrode disposed within said space in said body closely adjacent and in non-contacting relationship with said first membrane, said first electrode having a non-sintered layer of platinum black and polytetrafluoroethylene disposed thereon;
   e. a second electrode disposed within said space in said body in non-contacting relationship with said first electrode;
   f. an electrochemically inert hydrophilic filler material disposed within said space in said body and in contact with said first and second electrodes;
   g. an electrolytic material disposed throughout a portion of said filler material and being in contact with said first and second electrodes whereby an electrical path between said first and second electrodes is established through said electrolytic material;
   h. means adapted for providing an electrical connection operably connected to said first and second electrodes; and,
   i. means disposed adjacent said first membrane for causing an electrochemical reaction producing fluid to permeate said first membrane and contact said first electrode.

2. An electrochemical cell as claimed in claim 1 wherein said first electrode comprises:
   a. a noble metal screen;
   b. a layer of pressed platinum black;
   c. a non-sintered layer of platinum black and polytetrafluoroethylene disposed on said layer of pressed platinum black; and,
   d. a permeable layer of polytetrafluoroethylene disposed on said layer of platinum black and polytetrafluoroethylene.

3. An electrochemical cell comprising:
   a. a body having a space therein and two openings into said space, said body being of an electrochemically inert material;
   b. a first membrane disposed to cover one of said two openings in said body, said first membrane being of a highly porous electrochemically inert material;
   c. a second membrane disposed to cover the other of said two openings in said body, said second membrane being of highly porous electrochemically inert material;
   d. a first electrode disposed witin said space in said body closely adjacent and in non-circulating relationship with said first membrane;
   e. a second electrode disposed within said space in said body in non-contacting relationship with said first electrode;
   f. an electrochemically inert hydrophilic filler material disposed within said space in said body and in contact with said first and second electrodes;
   g. an electrolytic material disposed throughout a portion of said filler material and being in contact with said first and second electrodes whereby an electrical path between said first and second electrodes is established through said electrolytic material;
   h. means adapted for providing an electrical connection operably connected to said first and second electrodes;
   i. means disposed adjacent said first membrane for causing an electrochemical reaction producing fluid to permeate said first membrane and contact said first electrode; and,
   j. means disposed adjacent said first membrane for scrubbing the electrochemical reaction producing fluid of undesired components, said means for scrubbing being a permeable layer of silver oxide.

4. An electrochemical cell as claimed in claim 3 wherein:
said silver oxide is argentous oxide.

5. An electrochemical cell as claimed in claim 3 and additionally comprising:
means disposed adjacent said second membrane for scrubbing any fluid entering said space in said body through said second membrane of undesired components, said means for scrubbing being a permeable layer of palladium on carbon.

6. An electrochemical cell as claimed in claim 3 and additionally comprising:
means disposed adjacent said second membrane for scrubbing any fluid entering said space in said body through said second membrane of undesired components, said means for scrubbing being a low porosity membrane of polytetrafluoroethylene.

* * * * *